United States Patent [19]

Pert et al.

[11] Patent Number: 5,529,983
[45] Date of Patent: Jun. 25, 1996

[54] USE OF SMALL PEPTIDES IN THE TREATMENT OF PSORIASIS

[75] Inventors: Candace B. Pert; Michael R. Ruff, both of Bethesda, Md.; Lennart Wetterberg, Bromma, Sweden

[73] Assignee: The United States of America as represented by the Department of Health and Human Services, Washington, D.C.

[21] Appl. No.: 480,104

[22] Filed: Jun. 7, 1995

Related U.S. Application Data

[63] Continuation of Ser. No. 82,148, Jun. 28, 1993, abandoned, which is a continuation of Ser. No. 614,064, Nov. 14, 1990, abandoned, which is a continuation of Ser. No. 370,107, Jun. 21, 1989, abandoned, which is a continuation of Ser. No. 197,095, May 16, 1988, abandoned, which is a continuation of Ser. No. 940,919, Dec. 12, 1986, abandoned, which is a continuation-in-part of Ser. No. 869,919, Jun. 3, 1986, abandoned, and a continuation-in-part of Ser. No. 878,586, Jun. 26, 1986, abandoned, and a continuation-in-part of Ser. No. 933,374, Nov. 21, 1986, abandoned.

[51] Int. Cl.$^6$ ............................ A61K 38/08; C07K 7/06
[52] U.S. Cl. ............................ 514/16; 514/863; 530/328
[58] Field of Search ........................ 514/16, 863; 530/328

[56] References Cited

U.S. PATENT DOCUMENTS

| | | | |
|---|---|---|---|
| 4,520,113 | 5/1985 | Gallo et al. | 424/89 |
| 4,525,300 | 6/1985 | Yoshida et al. | 530/327 |
| 4,629,783 | 12/1986 | Cosand | 530/324 |

OTHER PUBLICATIONS

Day, How to write and publish a scientific paper, 2nd edition, isi press, Philadelphia, pp. 15–19 (1983).
Bridge et al., Proceedings of the 4th International AIDs Conference, Abst. #318 (1988).
Harris, Phoenix AIDS Research Meeting, Abstract, May, 1991.
Julander et al., Antiviral Chemistry & Chemotherapy vol. IC6), pp. 349–354 (1990).
MacFadden et al., VIIth Int'l Conference on AIDs, Florence, 1991.
Rudimger, Peptide Hormones, Parson (Ed.), U. Park Press, Baltimore pp. 1–7 (1976).
Fauci, PNAS, USA, vol. 83, pp. 9278–9283 (Dec. 1986).
Pert et al. Proc. Natl. Acad. Sci. USA vol. 83 pp. 9254–9258 (Dec. 1986).
Ruff et al., Chem. Abstr. vol. 106 No. 136804e (1987).
Wetterberg et al. Lancet, p. 159 (Jan. 17, 1987).

*Primary Examiner*—Christina Y. Chan

[57] ABSTRACT

The treatment of human patients suffering from Acquired Immune Deficiency Syndrome (AIDS) with therapeutic amounts of certain small peptides which specifically utilizes peptide T (Ala-Ser-Thr-Thr-Thr-Asn-Tyr-Thr), vasoactive intestinal polypeptide (VIP), or a core pentapeptide selected from a peptide of the following formula:

$$Thr-X-Y-Tyr-Thr$$

where

X and Y=any amino acid

γ=preferably Asp $Thr_1$ may be repalced by D-Ala

A preferred regimen for utilization of peptide T, a preferred peptide treating agent, is 1 mg twice daily for one week followed by 2 mg twice daily for three weeks, constituting an initial dosage regimen which may be repeated. This regimen has resulted in substantial increase in total white cell count assay, thus combatting the deleterious effect of the AIDS virus.

2 Claims, No Drawings

USE OF SMALL PEPTIDES IN THE TREATMENT OF PSORIASIS

This application is a continuation of application Ser. No. 08/082,148, filed Jun. 28, 1993, now abandoned; which is a continuation of application Ser. No. 07/614,064, filed Nov. 14, 1990, now abandoned; which is a continuation of application Ser. No. 07/370,107, filed Jun. 21, 1989, now abandoned; which is a continuation of application Ser. No. 07/197,095, filed May 16, 1988, now abandoned; which is a continuation of application Ser. No. 06/940,919, filed Dec. 12, 1986, now abandoned; which is a CIP of application Ser. No. 06/869,919, filed Jun. 3, 1986, now abandoned; and a CIP of application Ser. No. 06/878,586, filed Jun. 26, 1986, now abandoned; and a CIP of application Ser. No. 06/933,374, filed Nov. 21, 1986, now abandoned.

FIELD OF THE INVENTION

This invention relates to the treatment of human patients suffering from Acquired Immune Deficiency Syndrome (AIDS) with therapeutic amounts of certain small peptides which specifically utilizes peptide T (Ala-Ser-Thr-Thr-Thr-Asn-Tyr-Thr), vasoactive intestinal polypeptide (VIP), or a core pentapeptide selected from a peptide of the following formula:

Thr-X-Y-Tyr-Thr where

X and Y=any amino acid

Y=preferably Asp $Thr_1$ may be replaced by D-Ala

A preferred regimen for utilization of peptide T, a preferred peptide treating agent, is 1 mg twice daily for one week followed by 2 mg twice daily for three weeks, constituting an initial dosage regimen which may be repeated. This regimen has resulted in substantial increase in total white cell count assay, thus combatting the deleterious effect of the AIDS virus.

DEFINITION

In this application and claims the abbreviations for the amino acids are as follows:

ala, alanine; arg, arginine; asn, asparagine; asp, aspartic acid; cys, cysteine; gln, glutamine; glu, glutamic acid; gly, glycine; his, histidine; ile, isoleucine; leu, leucine; lys, lysine; met, methionine; phe, phenylalanine; pro, proline; ser, serine; thr, threonine; trp, tryptophan; tyr, tyrosine; val, valine.

BACKGROUND

The seriousness of the AIDS illness in human patients appears to be ever increasing and, although the etiological agent human T-cell lymphotropic virus Type III (HTLV-III) or human immunodeficiency virus (HIV) has been analyzed and assayed as in the Gallo U.S. Patent No. 4,520,113, no substantial checking of the illness has been shown. The present treatment of patients is with a treating agent of small peptides which have been proven to inhibit HIV infection in vitro as well as blocking the binding of the viral envelope to the CD4 receptor.

A preferred peptide treating agent is the octapeptide T, also known as Ala-Ser-Thr-Thr-Thr-Asn-Tyr-Thr and vasoactive intestinal polypeptide defined as His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn-$NH_2$.

MATERIAL INFORMATION DISCLOSURE

Pert, et al, *Proc. Natl. Acad. Sci. USA*, 23:9254–2958, 1986.

SPECIFIC DISCLOSURE

Toxicity. As to toxicity, the complete schedule of peptide therapeutic agents above gave negative evidence of toxicity. Specifically as tot the preferred Peptide T, which has relationship to VIP, the preliminary findings are that it was non-toxic with the exception of lowering the blood pressure on one occasion when the infusion rate was increased. The fall of blood pressure it was believed may be related to the Peptide T since it is homologous to a segment of vasoactive intestinal peptide.

As subsidiary matters related to toxicity, there has been an improvement of lymphocyte counts during the treatment period where patients had been previously treated with peptides. In one case a concomitant psoriasis improved during treatment.

THERAPEUTIC RESPONSE

Four patients were treated and are subject of this invention. They are noted Patients A, B, C, and D. The treatment was 1 mg of Peptide T twice a day by intravenous infusion over an hour period the first week. Weeks 2, 3 and 4 the patients received 2 mg twice daily administered in the same way. As to the therapeutic response measurement of total lymphocytes, the showing in A with increase of blood count was measured in this instance by total lymphocytes which is the most sensitive count available to register the diminution of the cytotoxic effect of AIDS virus. At the beginning of treatment the value was 0.09 and at the end of treatment was 0.67, denoting a seven-fold increase in lymphocyte count. All of the patients had increases in lymphocyte count of 2–3 fold.

It is noted in general where AIDS patients' lymphocyte count gets as low as 0.1, the patient becomes terminal very rapidly. Of the four patients selected, none of the patients' conditions deteriorated and in some the improvement was dramatic.

One patient, Patient A, had psoriasis all over his body, especially on the hands and arms and it started to clear up after the first four weeks. He went away and when he came back he was completely healed.

Another patient (B) had a persistent low grade fever for 5–6 months, which cleared up after a week on the peptide T treatment.

All four patients had three abnormalities according to the NMR. Three patients (A, B, and C) showed improvements in brain scans. The fourth patient's data has not been determined.

Patient D developed pneumocystis while he was waiting to start the trial. He was given the peptide T treatment and is improving.

Patient C had thrush or canditas of the mouth and it completely cleared up during four weeks of the peptide T treatment.

In humans there was no toxicity apparent in the liver or kidney.

[D-ala¹]peptide-T-amide was given twice daily intravenously to hamsters for six weeks. At the end of that time they were sacrificed and histologic studies were done on all organs; there was no significant difference. Liver enzymes and kidney enzymes were normal after injection.

We claim:

1. A method of alleviating symptoms of psoriasis associated with HIV infection comprising administering a psoriasis relieving effective amount of a peptide consisting of the sequence Ala-Ser-Thr-Thr-Thr-Asn-Tyr-Thr, wherein the terminal Thr is the carboxy end of the peptide.

2. The method of claim 1 wherein said peptide is administered by intravenous infusion.

* * * * *